United States Patent [19]

Hancock

[11] Patent Number: 5,371,234
[45] Date of Patent: Dec. 6, 1994

[54] ION SPECIFIC CHELATING AGENTS DERIVED FROM β-HYDROXYHISTIDINE, 4-(1-HYDROXY-1-ALKYL)IMIDAZOLE AND DERIVATIVES THEREOF

[75] Inventor: Diane K. Hancock, Rockville, Md.

[73] Assignee: The Unites States of America as represented by the Secretary of Commerce, Washington, D.C.

[21] Appl. No.: 949,215

[22] Filed: Sep. 23, 1992

[51] Int. Cl.$^5$ .................. C07D 233/90; C07F 19/00
[52] U.S. Cl. .................................. 548/339.1; 548/104; 548/106; 548/340.1; 548/341.1; 252/184; 534/13
[58] Field of Search ............. 548/339.1, 341.1, 340.1, 548/104, 106; 534/13; 252/184

[56] References Cited

U.S. PATENT DOCUMENTS

| | | | |
|---|---|---|---|
| 3,142,702 | 7/1964 | Sawa et al. | 548/339.1 X |
| 3,200,136 | 7/1966 | Grossmith | 556/183 |
| 3,391,176 | 7/1968 | Grossmith | 556/183 |
| 3,403,163 | 9/1968 | Fuchsman | 548/106 |
| 3,413,326 | 11/1968 | Schmid | 548/339.1 X |
| 3,968,120 | 7/1976 | Regel et al. | 548/104 X |
| 4,124,533 | 11/1978 | Knowles et al. | 548/339.1 X |
| 4,479,936 | 10/1984 | Vandenbergh et al. | 424/92 |
| 4,530,963 | 7/1985 | DeVoe et al. | 525/54.1 |
| 4,540,667 | 9/1985 | Orser et al. | 435/172.3 |
| 4,727,068 | 2/1988 | Abrams et al. | 514/184 |
| 4,872,899 | 10/1989 | Miller | 71/11 |

FOREIGN PATENT DOCUMENTS

| | | | |
|---|---|---|---|
| 71-01644 | 8/1971 | Netherlands | 548/104 |
| 1636414 | 3/1991 | U.S.S.R. | 548/107 |

OTHER PUBLICATIONS

Pyman, J. Chem. Soc. (London) vol. of 1911, pp. 668–675.
Chemistry in Britain, Jun. 1990, pp. 565–567, P. S. Dobbin et al.: "Iron chelation therapy".
Radiation Protection Dosimetry, vol. 26, No. 1/4, pp. 351–358 (1989), P. W. Durbin et al.: "Removal of $^{238}$Pu(IV) from Mice by Polycatechoylate, -Hydroxamate or -Hydroxypyridinonate Ligands".
Comments Agric. & Food Chem., 1987, Gordon and Breach Science Publishers S.A., Great Britain, vol. 1, No. 2., pp. 95–114, Bernard Schwyn et al., "Siderophores from Agronomically Important Species of the Rhizobiacae".
C&EN, May 2, 1977, Rebecca L. Rawlis: "Tailor-made drugs treat genetic blood disease".
Inorganica Chimica Acta, 94 (1984) 193–204, Kenneth N. Raymond et al.: "Actinide-Specific Complexing Agents: their Structural and Solution Chemistry".
Chem. Rev., vol. 89, No. 7, American Chemistry Society, pp. 1563–1579, Nov. 1989, Marvin J. Miller: "Syntheses and Therapeutic Potential of Hydroxamic Acid Based Siderophores and Analogues".
Annals of the Rheumatic Diseases, vol. 48, pp. 382–388, 1989, S. D. Hewitt et al.: "Investigation of the anti-inflammatory properties of hydroxypyridinones".
Environmental Inorganic Chemistry, pp. 331–347, 1985, VCH Publishers, Inc., Kenneth N. Raymond: "Specific Sequestering Agents for Iron and Actinides".
Critical Reviews in Toxicology, vol. 21, Issue 3, pp. 209–233, 1991, Mark M. Jones: "New Developments in Therapeutic Chelating Agents as Antidotes for Metal Poisoning".
Topics in Current Chemistry, 123, 49–102 (1984), Kenneth N. Raymond et al., "Complexation of Iron by Siderophores. A Review of Their Solution and Structural and Chemistry & Biological Function".

(List continued on next page.)

Primary Examiner—Floyd D. Higel
Attorney, Agent, or Firm—Stevens, Davis, Miller & Mosher

[57] ABSTRACT

β-hydroxyhistidine, 4-(1-hydroxy-1-alkyl)imidazole or derivatives thereof can be used as a bidentate ligand in the chelation of iron(III), Al(III), Cr(III), Ga(III) and the actinides(IV), such as plutonium 238. β-hydroxyhistidine is found in a pyoverdine-type siderophore produced by Pseudomonas fluorescens 244.

11 Claims, No Drawings

OTHER PUBLICATIONS

*Applied Microbiology*, vol. 26, No. 3, Sep. 1973, pp. 321–326, J. D. Nelson et al., "Biodegradation of Phenylmercuric Acetate by Mercury-Resistant Bacteria".

*The Journal of Antibiotics*, vol. XXIV, No. 11, Nov. 1971, pp. 795–796, Tomohisa Takita et al., "Chemistry of Bleomycin, V. Revised Structure of an Amine Component of Bleomycin $A_2$".

*The Journal of Antibiotics*, vol. XXX, No. 10, Oct. 1977, pp. 789–805, Masataka Konishi et al., "Tallysomycin, A New Antitumor Antibiotic Complex Related to Bleomycin. II. Structure Determination of Tallysomycins A and B".

*Biochemistry*, 1981, 20, 6446–6457, Martin Teintze, et al., "Structure of Ferric Pseudobactin, a Siderophore from a Plant Growth Promoting Pseudomonas ".

*The Journal of Biological Chemistry*, vol. 257, No. 14, Issue of Jul. 25, 1982, pp. 8086–8090, Stephen B. Philson et al., "Siderochromes from *Pseudomonas fluorescens*. II. Structural Homology as Revealed by NMR Spectroscopy".

*Iron Transport in Microbes, Plants and Animals*, Chapter 10, pp. 169–187, Pascal Demange et al., "Bacterial Siderophores: Structure and Physicochemical Properties of Pyoverdins and Related Compounds" (1983).

*Z. Naturforsch*, 45b, 1437–1450 (1990), G. Mohn, et al., "New Pyoverdin-Type Siderophores from *Pseudomonas fluorescens* [1]".

*Biochemistry*, 1990, 29, 11041–11051, Pascal Demange et al., "Bacterial Siderophores: Structures of Pyoverdins Pt, Siderophores of *Pseudomonas tolaasii* NCPPB 2192, and Pyoverdins Pf, Siderophores of *Pseudomonas fluorescens* CCM 2798. Identification of an Unusual Natural Amino Acid".

*Journal of the American Chemical Society*, 101:14, 3982–3983, Jul. 4, 1979, "Synthesis of L-erythro-$\beta$-Hydroxyhistidine from D-Glucosamine" Hecht et al.

*The Journal of Nuclear Medicine*, vol. 21, No. 10, 1980, pp. 935–939, Thomas Emery et al., "Siderophore-Mediated Mechanism of Gallium Uptake Demonstrated in the Microorganism *Ustilago sphaerogena*".

ION SPECIFIC CHELATING AGENTS DERIVED FROM β-HYDROXYHISTIDINE, 4-(1-HYDROXY-1-ALKYL)IMIDAZOLE AND DERIVATIVES THEREOF

The present invention relates to the use of a bidentate ligand as a chelating agent for, for example, iron. Specifically, the present invention relates to the use of β-hydroxyhistidine, 4-(1-hydroxy-1-alkyl)imidazole or derivatives thereof as a chelating agent.

BACKGROUND OF THE INVENTION

Diseases such as thalassemia which require repeated blood transfusions result in a build up of iron in the body which is deposited in the heart, liver, endocrine glands, as well as other organs. The iron overload, if not controlled, is fatal. To reduce iron overload the patient is treated with selective iron chelators, the usual one being desferrioxamine B (Desfetal). Unfortunately, Desfetal is orally inactive and treatment is difficult. Hence considerable effort has been expended in developing new iron(III) chelating agents that would be suitable for chelation therapy.

Numerous metal-ion chelators exist but unfortunately their lack of specificity often makes their use in chelation therapy more detrimental than beneficial. The microbial world however produces an array of low-molecular-weight molecules whose specific purpose is to bind iron(III), desferrioxamine is in fact one of them. These ferric-ion chelators, termed siderophores (Gr. "iron bearer"), for the most part contain three bidentate ligands, which octahedrally bind the metal ion. The bidentate ligands found in the siderophores are quite limited in number. They are hydroxamic acid (as in desferrioxamine), catechol, occasionally β-hydroxyaspartic acid, and in one case hydroxypyridinone. These bidentate ligands have been used as models for the design of new iron-chelating drugs. See Dobbin et al, "Iron Chelation Therapy", *Chemistry in Britain*, pages 565–57, June, 1990 (the entire disclosure of which is incorporated by reference herein).

Pseudomonas and Azotobacter species often produce pyoverdine (also termed pseudobactin or azobactin)-type siderophores which consist essentially of the same yellow-green fluorescent chromophore, identified as 2,3-diamino-6,7-dihydroxyquinoline, linked to the N-terminus of an oligopeptide of six to twelve amino acids. Structures of many pyoverdines have been reported. Although these siderophores are strain specific, with differing amino acid composition and sequence, each, with the exception of the present case, contains the same limited range of three ferric-specific bidentate ligands: (1) the catechol group of the chromophore, (2) a hydroxamic acid, $N^\delta$-hydroxyornithine, present in cyclized form or as a formyl or acetyl derivative, and (3) an additional hydroxamic acid or a β-hydroxyaspartic acid. These bidentate groups octahedrally bind the ferric ion through oxygen atoms.

The use of β-hydroxyhistidine as in the present application is not disclosed or suggested by the prior art. U.S. Pat. No. 3,200,136 to Grossmith relates to chelates consisting of α-hydroxy-carboxylic acids with magnesium, aluminum and iron and are suggested for use as antacids or for the treatment of iron deficiencies in plants or animals. U.S. Pat. No. 3,391,176 to Grossmith relates to chelates formed from salicylato bidentate or 5-hydroxysalicyato ions with or without additional carboxylic acids (tartaric, citric or α-hydroxy) and aluminum, magnesium, iron or calcium, which were tested for analgesic and antipyretic activity. In U.S. Pat. No. 4,479,936, *Pseudomonas putida* NRRL-B-12537, isolated from soil adjacent to an oil well, is proposed as a plant growth protector by virtue of its ability to suppress phytopathogenic microorganisms. Prior art has established similar behavior for *Pseudomonas fluorescens* B10 by virtue of the siderophore produced by this species. The structure of the B-10 pseudobactin siderophore is known. See, for example, *Biochemistry*, volume 20, pages 6446–57 (1981), the entire disclosure of which is incorporated by reference herein. Thin layer chromatography was used to indicate that the siderophores produced by these two species were in fact different, but no structural information regarding the NRRL-B-12537 is presented. Although the structure of NRRL-B-12537 is not given, it is known in the art that the peptide moiety of pyoverdines and pseudobactins generally differ from strain to strain.

U.S. Pat. No. 4,520,963 to DeVoe provides specific examples of waste treatment and metal recovery with respect to potential applications of the β-hydroxyhistidine ligand of the present application. Although DeVoe may initially (column 6, lines 48–52) imply that the proposed use of organic chelating compounds includes "any suitable functional derivatives, analogs or enantioforms" of microbial siderophores, some examples of which are listed, nothing therein discloses or suggests a chelating agent comprising β-hydroxyhistidine or any other imidazole derivative, as in the present invention. U.S. Pat. No. 4,540,667 to Orser deals specifically with the fluorescent siderophores from *Pseudomonas syringae*, not *Pseudomonas fluorescens* 244, as in the present invention. U.S. Pat. No. 4,727,068 to Abrams relates to ferrocene related iron (III) complexes. U.S. Pat. No. 4,872,899 to Miller relates to the treatment of plant chlorosis using rhodotorulic acid, a hydroxamate siderophore. The entire disclosures of the aforementioned U.S. patents are all expressly incorporated, in their entireties, by reference

SUMMARY OF THE INVENTION

An object of the present invention is to provide a new bidentate ligand for use in a chelating agent.

Another object of the present invention is to provide such a chelating agent.

A further object of the present invention is to provide a new bidentate ligand that is acid stable and could therefore be used in the design and synthesis of new oral chelation therapy agents containing this bidentate ligand or derivatives of this bidentate ligand.

A fourth object of the present invention is to provide a method of chelating iron(III), Al(III), Cr(III), Ga(III) and the actinides(IV), such as Plutonium 238.

These objects are accomplished by the use of a bidentate ligand found in a unique pyoverdine-type siderophore produced by *Pseudomonas fluorescens* 244 which has been deposited at the American Type Culture Collection, No. ATCC 33230, deposited with the American Type Culture Collection, 12301 Parklawn Drive, Rockville, Md. 20852-1776 on Feb. 11, 1980. The formula of the component amino acid that contains the bidentate ligand is:

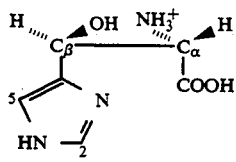

where the coordinating site is:

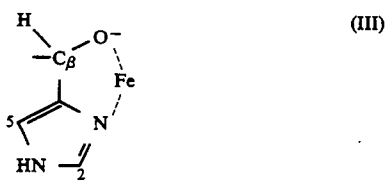

DETAILED DESCRIPTION OF THE PRESENT INVENTION

As discussed above, various different siderophore from many different sources are known in the art.

*Pseudomonas fluorescens* 244, however, expresses a highly unusual pyoverdine when it is grown in a chemically defined iron-poor medium. Mass spectrometry, NMR, and amino acid analysis were used to determine the structure of this novel siderophore, pyoverdine Pf244.

The presence of β-hydroxyhistidine was originally suggested by fast atom bombardment mass spectrometry (FABMS) of the intact pyoverdine and of a fully $^{15}$N-labelled preparation of the pyoverdine, and by NMR of the unlabelled material. Analysis of the observed sequence ions in the FABMS spectrum showed the presence of a residue with a mass of 153 atomic mass units (u) for the nonlabelled material and 156 u for the $^{15}$N-labelled material corresponding to the β-hydroxyhistidine and indicating the presence of three nitrogens in the residue. In addition to the peptide backbone fragmentation, fragment ions resulting from homolytic cleavage of the β-OH from the β-hydroxyhistidine subjected to partial acid hydrolysis (30 and 120 minutes at 105° C., 6 mol/L HCl) further substantiated the presence of the β-hydroxyhistidine residue and the peptide sequence: seryl-lysyl-β-hydroxyhistdyl-threonyl-seryl-cyclo-N$^\delta$-hydroxyornithine.

COSY NMR experiments on the intact pyoverdine revealed a spin system that also suggested the presence of the β-hydroxyhistidine residue. $^{13}$C NMR of pyoverdine Pf244 further supported the identity of this amino acid residue.

Amino acid analysis of phenylisothiocyanate (PITC) derivatized pyoverdine acid hydrolysate and an authentic sample of PITC derivatized DL-erthro-β-hydroxyhistidine proved that the unknown amino acid was not the erythro-isomer. A pure standard sample of the threo-isomer was not available, but 1 mg of the threo-isomer was recovered as a 2:1 mixture with the erythro-isomer from the spent mother liquors of the erythro synthesis. NMR analysis of the mixture verified its isomeric ratio and purity. PITC derivatization of this preparation and HPLC analysis confirmed the identity of the threo-isomer in pyoverdine Pf244.

The threo-amino acid was determined to be the L-enantiomer from the reactions of D- and L-amino acid oxidases (DAO and LAO) with pyoverdine hydrolysates and subsequent amino acid analysis of the reaction products derivatized with the chiral reagent, β-D-glucopyranosyl isothiocyanate tetraacetate (GITC).

Consideration of the pyoverdine Pf244 amino acid composition suggests that the β-hydroxyhistidine moiety serves as one of the bidentate chelating groups, the chromophore catechol and the cyclo-N$^\delta$-hydroxyornithine hydroxamic acid groups serving as the other two. Initial speculation that the chelation occurs though the β-hydroxy oxygen atom and the N-3 nitrogen atom of the β-hydroxyhistidine residue appears to be substantiated by the large shifts observed in the $^1$H and $^{15}$N NMR spectra on chelation of the pyoverdine and the $^{15}$N-labeled pyoverdine with Ga(III).

That is, a new amino acid β-hydroxyhistidine has been found in pyoverdine Pf244. Not only is this an amino acid hitherto unreported as occurring in nature, it also appears to be one of the ligands which bind the siderophore to the ferric ion. Siderophore bidentate ligands, which are very limited in number, have been used as models for the design of new iron-chelating drugs, hence, the occurrence of this new iron(III) ligand suggests, particularly in light of its acid stability, that it may have significant potential in the design and synthesis of new chelating agents for removal of excess iron, aluminum or $^{238}$Pu(IV) in chelation therapy and perhaps for metal removal or recovery and hazardous waste treatment. These agents can be administered to a patient orally or parenterally in amounts sufficient to reduce overload of iron, Al, Ga, Cr and/or the actinides, particularly plutonium, and can be mixed with acceptable chelator agent carriers.

Although siderophores are quite specific to ferric-iron, they will also chelate other ions that have nearly the same charge to ionic radius ratio as Fe(III) has. Among these ions are Al(III), Cr(III), Ga(III), and the actinides(IV). Hence, the bidentate ligands observed in siderophores have also been used as models in efforts to develop actinide(IV) sequestering agents. See Durbin et al., "Removal of $^{238}$Pu(IV) from Mice by Poly-Catechoylate, -Hydroxamate, or -Hydroxypyridinonate Ligands", *Radiation Protection Dosimetry*, volume 26, pages 351–58, (1989)(the entire disclosure of which is hereby incorporated by reference herein). These agents have been designed for chelation therapy of contaminated workers in order to remove radioactive materials, such as $^{238}$Pu(IV), which present carcinogenic risks.

Work on the structure elucidation of the pyoverdine-type siderophore produced by *Pseudomonas fluorescens* 244 has revealed the presence of a new amino acid. L-threo-β-hydroxyhistidine of the formula

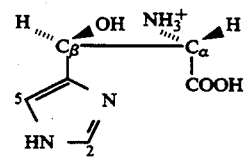

which appears to function as a bidentate ligand in the chelation of iron(III) ion. This finding suggests that the threo-β-hydroxyhistidine moiety may be added to the limited number of known bidentate ligands that function in the chelation of iron(III) and other metal ions with similar charge to ionic radius ratios. Hence, the threo-β-hydroxyhistidine ligand may prove to be a significant new model for developing new chelating materials for use in chelation therapy, waste clean-up, and other areas where specific metal-ion chelation is needed.

Structural models of the β-hydroxyhistidine moiety indicate that the erythro-isomer and the D- and L-enantiomers of both the threo- and erythro-isomers should bind iron(III) as well as other ions with similar charge to ionic radius ratios. Both the threo- and erythro-β-hydroxyhistidines can be used in either L or D form in the present invention.

Furthermore, since the chelating action of the β-hydroxyhistidine resides in the imidazole ring and the adjacent hydroxyl group, the present invention includes bidentate ligands composed of 4-(1-hydroxy-1-alkyl)imidazole and its derivatives.

Although the foregoing invention has been described in some detail by way of illustration, such detail is not intended to exclude the possibility that certain changes and modifications may be made within the scope of the claimed invention.

What is claimed:

1. A chelating agent comprising a chelatingly effective amount of a bidentate ligand selected from the group consisting of a β-hydroxyhistidine, 4-(1-hydroxy-1alkyl)imidazole and derivatives thereof in which there is an imidazole nitrogen in position 3 with a C—OH or C—O⁻ attached at the 4 position of the imidazole ring and an acceptable carrier.

2. The chelating agent of claim 1, wherein the bidentate ligand is a β-hydroxyhistidine or a derivative thereof.

3. The chelating agent of claim 1, wherein the bidentate ligand is 4-(1-hydroxy-1-alkyl)imidazole or a derivative thereof.

4. The chelating agent of claim 2, wherein the β-hydroxyhistidine is threo-β-hydroxyhistidine or a derivative thereof.

5. The chelating agent of claim 4, wherein the threo-β-hydroxyhistidine is L-threo-β-hydroxyhistidine or a derivative thereof.

6. The chelating agent of claim 4, wherein the threo-β-hydroxyhistidine is D-threo-β-hydroxyhistidine or a derivative thereof.

7. The chelating agent of claim 2, wherein the β-hydroxyhistidine is erythro-β-hydroxyhistidine or a derivative thereof.

8. The chelating agent of claim 7, wherein the erythro-β-hydroxyhistidine is L-erythro-β-hydroxyhistidine or a derivative thereof.

9. The chelating agent of claim 7, wherein the erythro-β-hydroxyhistidine is D-erythro-β-hydroxyhistidine or a derivative thereof.

10. A chelating agent comprising a chelatingly effective amount of an β-hydroxyhistidine produced from *Pseudomonas fluorescens* 244 and an acceptable carrier.

11. A chelating agent according to claim 10, wherein the β-hydroxyhistidine is of the formula:

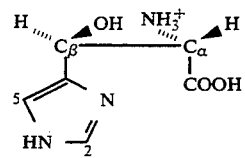

* * * * *